(12) United States Patent
Dragan et al.

(10) Patent No.: US 6,585,511 B2
(45) Date of Patent: Jul. 1, 2003

(54) DENTAL MATERIAL CONTAINER WITH POROUS FLOW THROUGH APPLICATOR

(75) Inventors: William B. Dragan, Easton, CT (US); John J. Discko, Trumbull, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 09/906,369

(22) Filed: Jul. 16, 2001

(65) Prior Publication Data

US 2003/0013066 A1 Jan. 16, 2003

(51) Int. Cl.$^7$ .................................................. A61C 5/04
(52) U.S. Cl. ......................... 433/90; 401/176; 401/177
(58) Field of Search ..................... 433/90, 89; 401/176, 401/177, 196, 207; 604/2, 3, 1; 132/320

(56) References Cited

U.S. PATENT DOCUMENTS

| | | | | |
|---|---|---|---|---|
| 3,481,676 A | * | 12/1969 | Schwartzman | 604/3 |
| 3,519,364 A | * | 7/1970 | Truhan | 604/2 |
| 4,218,155 A | * | 8/1980 | Weidner | 401/196 |
| 4,432,749 A | * | 2/1984 | Snyder et al. | 604/2 |
| 4,875,602 A | * | 10/1989 | Chickering et al. | 401/177 |
| 4,997,371 A | | 3/1991 | Fischer | |
| 5,122,056 A | * | 6/1992 | Barbee | 433/90 |
| 5,816,804 A | | 10/1998 | Fischer | |
| 5,829,976 A | * | 11/1998 | Green | 433/89 |
| 6,059,570 A | | 5/2000 | Dragan et al. | |
| 6,099,307 A | | 8/2000 | Discko, Jr. | |
| 6,202,897 B1 | * | 3/2001 | Martin et al. | 433/90 |
| 6,283,933 B1 | * | 9/2001 | D'Alessio et al. | 604/3 |
| 6,382,972 B1 | * | 5/2002 | Fischer et al. | 433/90 |

* cited by examiner

Primary Examiner—Todd E. Manahan
(74) Attorney, Agent, or Firm—Fattibene and Fattibene; Paul A. Fattibene; Arthur T. Fattibene

(57) ABSTRACT

A dental nozzle, cartridge, capsule or container having a porous or foam flow through applicator connected at the discharge end thereof; and having a body portion containing or receiving a low viscosity dental material. In one form, a displaceable plunger or piston is disposed within the body portion to extrude the dental material through the discharge orifice and attached flow through applicator. The foam or porous applicator may be connected to the discharge end at the time of manufacture as by molding, or by mechanically connecting or by adhering the same to the discharge orifice as part of the assembly process. The flow through applicator may be made in a variety of shapes to provide improved and controlled application of a low viscosity dental material to a dental site. Additionally, the porosity of the porous or foam material may be matched to the viscosity of the dental material to control the flow of dental material therethrough.

15 Claims, 4 Drawing Sheets

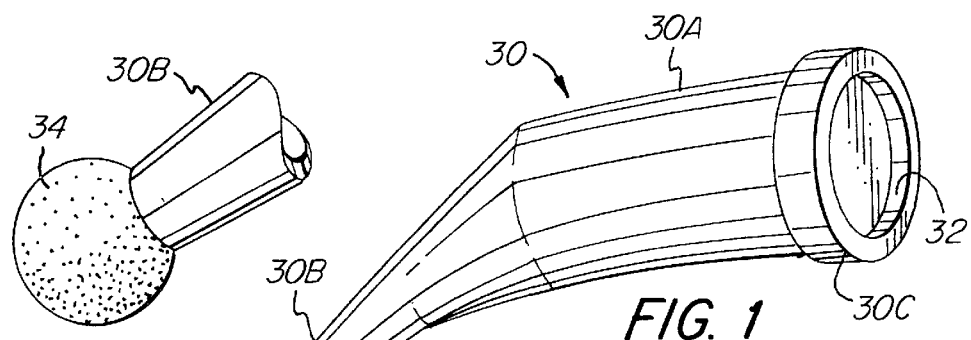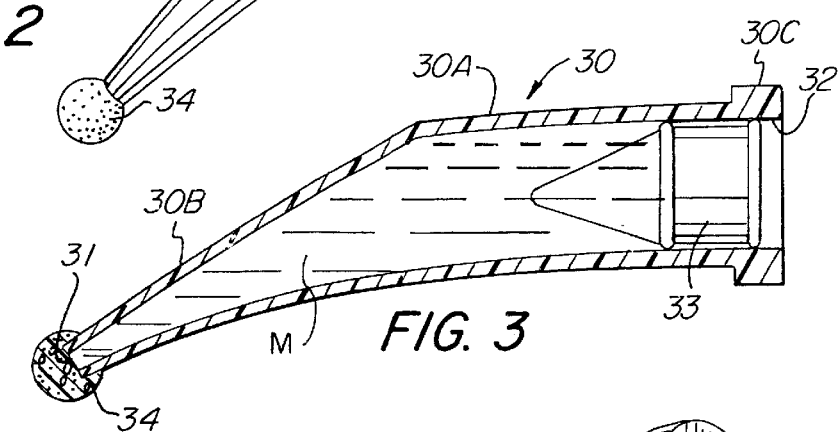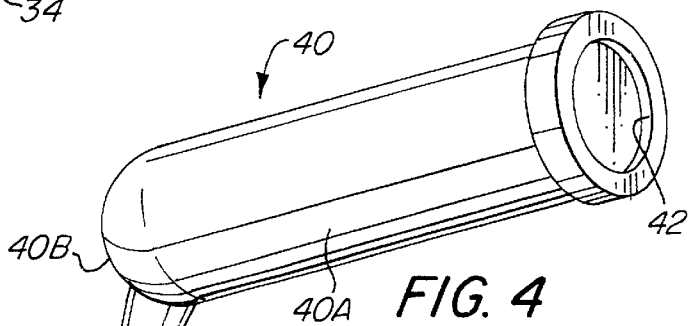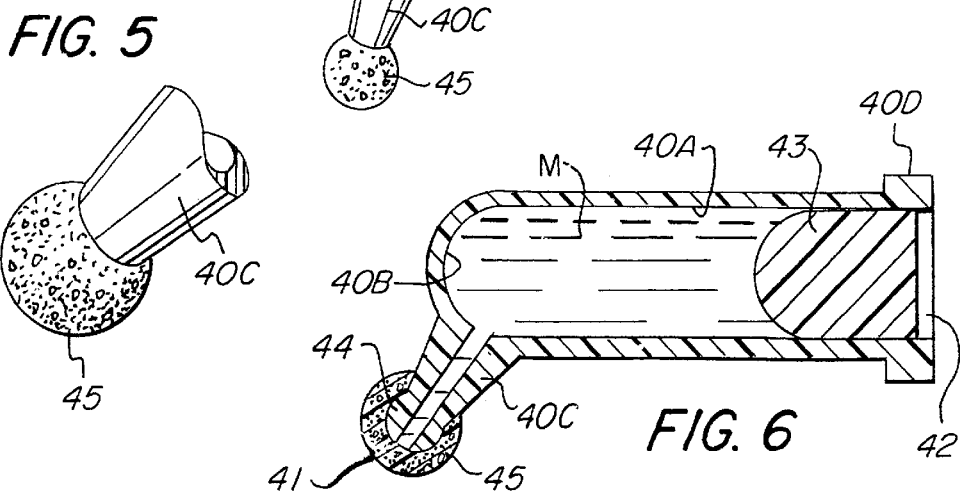

DENTAL MATERIAL CONTAINER WITH POROUS FLOW THROUGH APPLICATOR

FIELD OF THE INVENTION

The invention relates generally to a dental container, capsule or nozzle used for applying relatively low viscosity or fluent dental materials onto a tooth, and more particularly to a capsule, nozzle or container for dispensing low viscosity dental material through a porous flow through applicator connected to the discharge orifice for evenly distributing and applying the low viscosity or fluent dental material directly onto a tooth as the material is being dispensed.

BACKGROUND OF THE INVENTION

Heretofore, high viscosity dental materials have been applied with the use of a dental capsule utilizing a displaceable piston or plug to force or express a high viscosity material out from the capsule through a discharge orifice. A syringe having a plunger is often used in combination with such capsule to displace the piston. In many dental applications, when a relatively low viscosity or very fluent material is to be applied, brushes have been used to apply the same. However, using a brush type applicator requires constant reapplication of the dental material to the brush. This is inconvenient and time consuming, and at times results in dripping or the placement of such low viscosity or fluent dental material in an inappropriate or even dangerous locations within the mouth. For example, various low viscosity dental materials, such as acid etch materials, are intended to be applied only to the tooth and may cause injury to the gum or other soft tissues if applied thereto.

Efforts have been made to overcome the problems encountered in the placement of low viscosity or fluent materials. One example of a dental dispenser or syringe for use in applying dental materials is disclosed in U.S. Pat. No. 5,816,804 entitled "Fiber Ended Open Orifice Delivery Tip" issuing to Fischer on Oct. 6, 1998. Therein disclosed is a delivery syringe having a plurality of small fibrous bristles disposed around an outer periphery of the nozzle adjacent the discharge orifice.

U.S. Pat. No. 6,059,570 entitled "Dental Container Type Applicator" granted to Dragan et al on May 9, 2000, which is herein incorporated by reference, discloses a dental container, capsule or nozzle that has minute fibers or flocking adhered about the external surface of a discharge nozzle in the vicinity of the discharge orifice, which permits the user to spread, burnish, or distribute dental material on a tooth as the material is being expressed from the capsule, nozzle or container.

While these prior applicator devices are suitable for applying certain dental materials, some difficulty has been encountered in achieving the desired control or consistent flow requirements often required in effecting proper tooth restoration and/or in performing other dental procedures requiring the use of low viscosity materials. Additionally, the difficulty in the placement of the minute or small fibers or bristles onto a nozzle has often resulted in irregular covering of such fibers onto the nozzle or discharge end of a cartridge to result in the possibility of scratching or damaging the surface on which the material is to be applied. Therefore, there is a need for an improved, more easily manufactured and more reliable dental applicator for use in applying materials of relatively low viscosity by which such materials can be spread, burnished or distributed directly onto a tooth or other surface as the material is being dispensed from a capsule or syringe.

SUMMARY OF THE INVENTION

The invention is directed to a dental container, nozzle, or capsule for containing or dispensing a low viscosity dental material which includes a discharge end or orifice having a foam or porous flow through applicator or covering. In one embodiment the dental container includes a needle-like cannula through which the material is dispensed. The foam or porous flow through covering or applicator attached to the discharge end or orifice may take a variety of different shapes suitable for performing a prescribed procedure. The foam or porous covering is uniformly formed or connected to the discharge end for permitting an even, uniform flow of the dental material therethrough, as the material is being dispensed. The foam or porous flow through covering may be applied to the container or capsule during the molding process thereof and can be molded to any desired shape. In another embodiment, the foam or porous covering may be mechanically retained or adhered by suitable adhesive onto the discharge end of a capsule or cartridge.

Accordingly, it is an object of the present invention to provide an improved applicator for the application of low viscosity dental materials directly onto a tooth.

It is a further object of the present invention to provide a dental applicator having improved material flow characteristics.

It is an advantage of the present invention that the porous applicator end may be made in a variety of different shapes depending upon the dental procedure to be performed.

It is a further advantage of the present invention that the dental container or cartridge with flow through applicator can be produced with consistency and uniformity.

A feature of the present invention is that a foam or porous flow through cover is connected to the discharge end of the dental container or capsule to control the dispensing and application of a fluent or low viscosity dental material.

It is a further feature of the present invention that the discharge end of a dental capsule or cartridge may be of various shapes suitable for a particular procedure.

These and other objects, advantages, and features will become readily apparent in view of the following more detailed description.

BRIEF DESCRIPTION OF THE DRAWINGS

FIG. 1 is a perspective view of an embodiment of the present invention.

FIG. 2 is a partial view of the applicator or discharge end of the embodiment illustrated in FIG. 1.

FIG. 3 is a side elevational view in cross section of an embodiment of the present invention.

FIG. 4 is a perspective view of another embodiment of the present invention.

FIG. 5 is a partial view of the applicator or discharge end of the present invention illustrated in FIG. 4.

FIG. 6 is a side elevational view in cross section of another embodiment of the present invention.

DETAILED DESCRIPTION OF THE PREFERRED EMBODIMENTS

Figure 7:
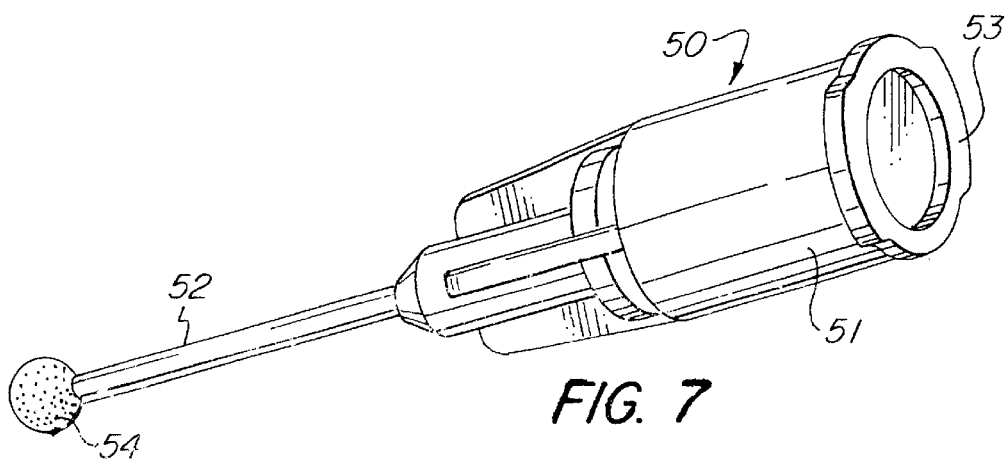
FIG. 7 is a perspective view of another embodiment of the present invention.

FIGS. 1–3 illustrate one embodiment of the present invention. FIGS. 1 to 3 illustrate a dental capsule 30 which is formed from any suitable plastic material having a generally cylindrical body portion 30A. The cylindrical body portion 30A defines a reservoir for containing a predetermined amount of relatively non-viscous, a low viscosity, or fluid dental material M. The dental material may comprise a sealant, cement, bonding agent, flowable composite or other dental material having a generally low viscosity or fluent consistency. The dental capsule or cartridge 30 has a rear open end 32 and an opposite discharge end 31. A flange 30C is placed adjacent the rear open end 32. A piston 33 is freely displaceable within the body portion 30A and seals opening 32. The tapering discharge nozzle end 30B provides a relatively smooth transition zone from the larger diameter body portion 30A to the smaller diameter discharge orifice 31. Attached to the discharge nozzle 30B and surrounding the orifice 31 is a covering 34 of a porous material such as a sponge, open cellular foam, or the like, by which the material being dispensed can flow therethrough and by which the material may be spread, burnished or brushed directly onto a tooth as it is being dispensed. The open cellular covering 34 may be formed by molding the same during the molding of the capsule or cartridge 30, or may be attached thereto by a suitable adhesive or by mechanical means. When molded, the open cellular covering 34 bonds to the discharge nozzle without the need for glue or adhesive. The covering 34 may be made of any cellular or foam-like material that is porous, e.g. a natural or synthetic sponge, plastic foam or other open cellular or porous material. The porosity of the covering 34 may be matched to the viscosity of the material M. That is, if the material M being dispensed is somewhat less fluent, the foam or covering 34 may be provided with larger pores or openings so as to permit such less fluent material to flow therethrough in a controlled manner. If the material M being dispensed is less viscous, the covering 34 may be formed with smaller openings or pores to control the flow therethrough. Therefore, the flow characteristics of the material M may be controlled accurately and in a consistent manner depending upon the viscosity of the material being dispensed therethrough.

FIGS. 4–6 illustrate another embodiment of the present invention. In this embodiment, a cartridge or capsule 40 comprises an elongated cylinder body portion 40A defining a reservoir for containing a supply of low viscosity dental material M. An end wall 40B is formed at one end, which is illustrated as being hemispherical. However, it will be understood that the end wall 40B may take other shapes well known and/or as disclosed in a number of prior capsule patents. Adjacent the end wall 40B and extending at an angle relative to the central axis of the body portion 40A is a discharge nozzle 40C. The discharge nozzle or cannula 40C communicates with the body portion 40A. The nozzle 40C terminates in a ball tip or sphere 44 which includes a discharge orifice 41. A displaceable piston 43 is placed at the open end 42 for sealing the open end 42 and for extruding the dental material when displaced. A flange 40D generally circumscribes the open end 42. A porous cover or applicator 45 is secured about the small sphere 44 at the end of the discharge nozzle 40C. The small sphere 44 provides support for the porous cover 45 and facilitates the spreading or brushing of the dental material onto a tooth surface.

FIG. 7 illustrates another embodiment of the present invention. In this embodiment, the dental tip, cartridge or capsule 50 is utilized as a delivery nozzle which may be directly attached to the end of a syringe (not shown) containing a quantity of low viscosity material to be dispensed through the dental tip 50. The dental tip 50 comprises a body portion 51 and a connected needle-like cannula 52 having a bore 56. The cannula 52 is connected to one end of the body 51 through which the dental material is discharged. A Luhr locking flange 53 is formed on the other end of the body 51. The Luhr locking flange 53 is constructed to releaseably mate and lock the tip 50 onto the end of a syringe, not shown, or other container defining a reservoir for the dental material. The needle cannula 52 is generally formed of metal, but can also be made of any suitable material, such as plastic. The cannula 52, when formed of metal, is preferably formed of a ductile metal which can be bent so that the discharge end or orifice may be disposed at any desired angle relative to the longitudinal axis of the body 51. A foam or porous flow through cover 54 is attached to the cannula 52. The flow through cover or applicator may be made of any type of porous material that has the desired porosity as hereinbefore described. In the illustrated embodiment, the porous covering 54 is illustrated as being spherical in shape.

Figure 8:
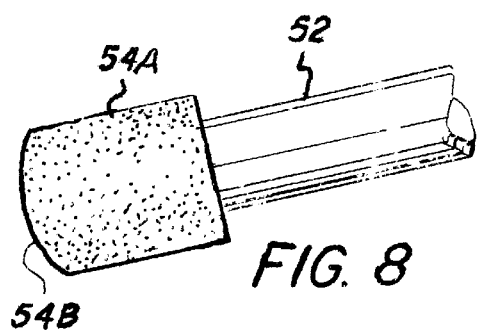
FIG. 8 is a partial view of the discharge or applicator end of another embodiment of the present invention.

FIG. 8 illustrates another embodiment of the present invention similar to that illustrated in FIG. 7. However, FIG. 8 illustrates only the applicator or discharge end of the embodiment. Attached to cannula 52 is a porous cover in the shape of a cylindrical shaped applicator circumscribing the discharge orifice 52A. The cylindrical applicator of foam or flow through cellular material 54A is provided with a recessed portion 58 by which it is fitted to the orifice end 52A of the cannula 52. The foam cylindrical applicator 54A may have a curved surface 54B formed at distal end.

Figure 9:
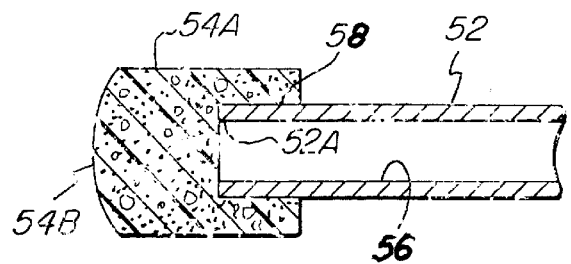
FIG. 9 is a cross sectional view of the applicator end or discharge end of the embodiment illustrated in FIG. 8.

FIG. 9 illustrates the embodiment illustrated in FIG. 8 in cross section. The foam cylindrical applicator 54A is attached to the cannula 52 as hereinbefore described. The recessed end portion 58 may be coated with a suitable adhesive so that the cylindrical applicator 54A is securely attached thereto. The foam cylindrical applicator 54A is snugly fitted to the end of the bore 56 of the cannula 52. Accordingly, dental material may freely flow from the orifice 52A and through the porous or foam cylindrical applicator 54A.

Figure 9A:
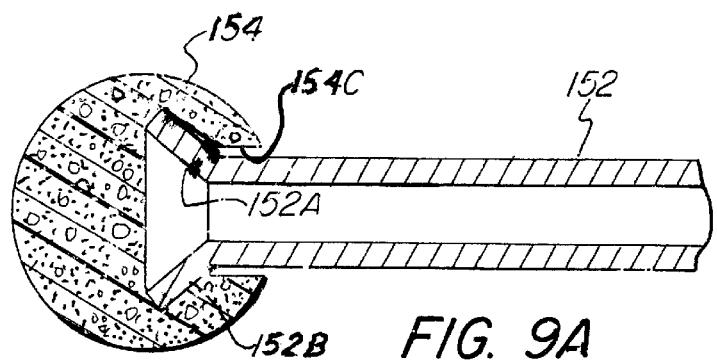
FIG. 9A is a cross sectional view of a discharge portion of another embodiment of the present invention.

FIG. 9A illustrates an embodiment of the present invention having a mechanical holding feature for attaching the foam or porous covering or applicator 154 to the cannula 152.

A cannula 152, which may be made of plastic or metal, is attached to a body portion of the capsule or cartridge as hereinbefore described. In the illustrated embodiment, the cannula 152 has an outwardly flare or mechanical retainer 152A formed at the discharge end. The foam applicator or cover 154 has a complementary shaped internal cavity 152B. The internal cavity 152B need only have a complementary shape to that of the flared retainer 152A so as to mechanically retain the foam applicator 154 onto the flare or mechanical retainer 152A of the cannula 152. For additional securement, a glue or suitable adhesive may also be used. The resiliency of the foam applicator 154 helps to hold the foam cover 154 on the cannula 152 which, in FIG. 9A, the cover 154 is illustrated as having a spherical shape. However, it will be understood that the shape may vary depending upon the use thereof. Additionally, the mechanical retainer 152A may have other desired shapes as long as the shape functions to mechanically hold the foam or porous flow through applicator 154 onto the cannula 152. The embodiment of FIG. 9A has the further advantage that different shaped foam applicators 154 may be selected for placement onto the discharge end of cannula 152, depending upon the application or preference of the user.

Figure 10:
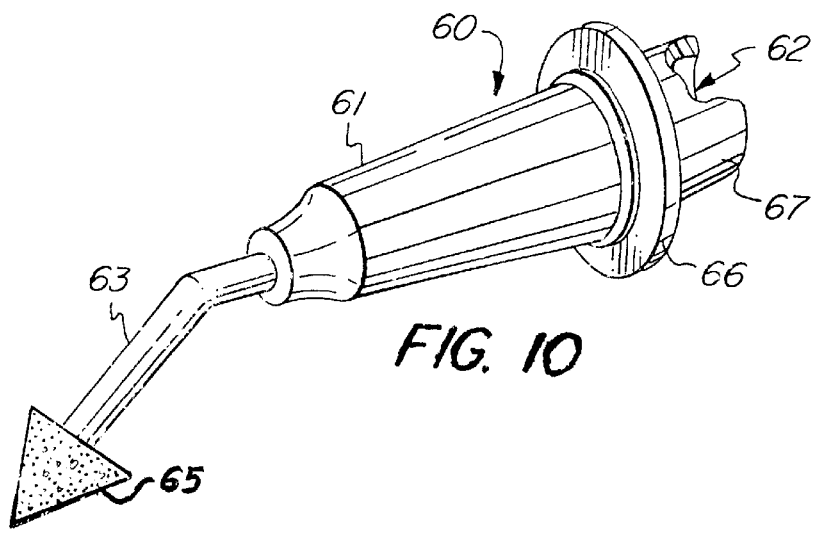
FIG. 10 is a perspective view of yet another embodiment of the present invention.

FIG. 10 illustrates another embodiment of the present invention. In FIG. 10, a dental cartridge, capsule or tip 60 includes a body portion 61 provided with a rear opening 62 at one end and a needle-like cannula 63 connected to the other end thereof. At the end of the needle like cannula 63 is a foam or porous flow through cover in the form of a cone defining an apex 65. The conically shaped cover 65 may be adhered to the cannula 63 by any of the means hereinbefore described. The tip 60 has a flange 66 and a nipple portion 67 adjacent thereto. The dental tip 60 is formed so as to be detachably connected to a syringe or container containing the dental material. It will be understood that the foam end 65 may assume other desired shapes. The conical shape terminating in a pointed apex provides for precise placing of the dental material flowing through the applicator end 65.

Figure 11:
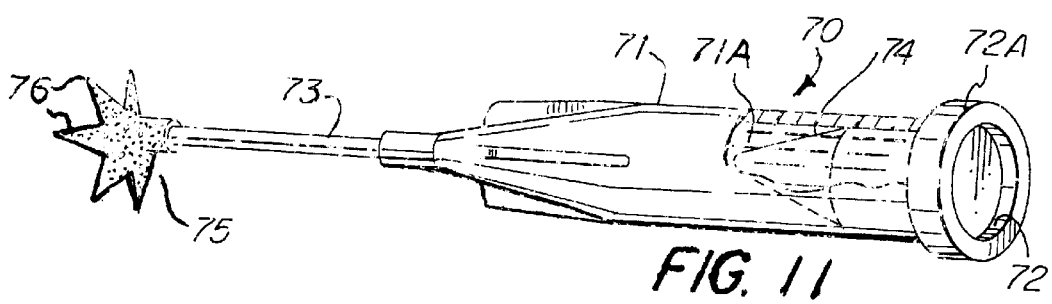
FIG. 11 is a perspective view in partial section of yet another embodiment of the present invention.

FIG. 11 illustrates yet another embodiment of the present invention. The dental capsule 70 is illustrated as having an elongated cylindrical body portion 71 which has an open end 72 and an elongated needle like cannula 73 at the other end. An outwardly extending flange 72A circumscribes the open end 72. A displaceable piston 74 seals the open end 72. A reservoir 71A contains low viscosity dental material. Attached to the discharge end of cannula 73 is a foam or porous flow through applicator 75. The foam or flow through applicator 75 is formed with a plurality of fingers or points 76.

Figure 12:
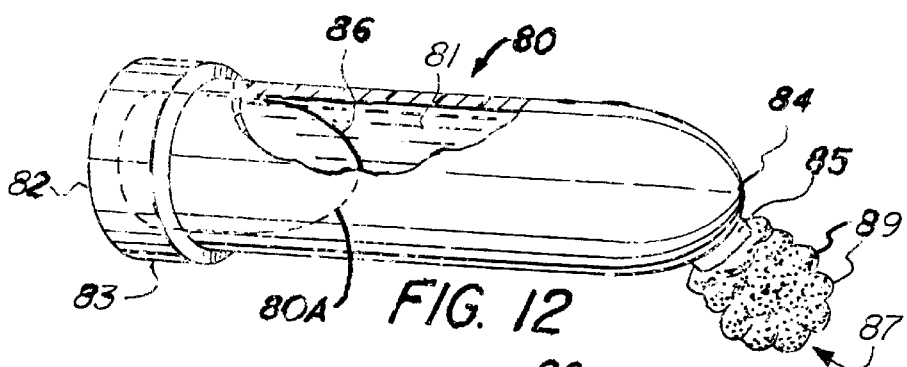
FIG. 12 is a perspective view with a partial section of yet another embodiment of the present invention.

FIG. 12 illustrates yet another embodiment of the present invention. The dental capsule, cartridge or tip 80 comprises an elongated, cylindrical or tubular body 80A defining a reservoir 81 for containing a predetermined amount of low viscosity dental material. One end of the body 80A has an opening 82. A radially extending flange 83 circumscribes opening 82. The other end of the body 80A is provided with a conical end wall 84. Extending at an angle relative to the end wall 84 is a discharge nozzle 85 having a discharge orifice. The displaceable piston 86 is provided with a conical shape end which complements the interior configuration of the end wall 84 and seals opening 82. A shaped foam or porous flow through applicator 87 is attached to the orifice end of the discharge nozzle 85. The shaped foam applicator 87 has a plurality of appendages 89 formed thereon. These appendages 89 assist in spreading or coating the dental material onto a tooth or other dental surface as the dental material is dispensed therethrough.

Figure 13:
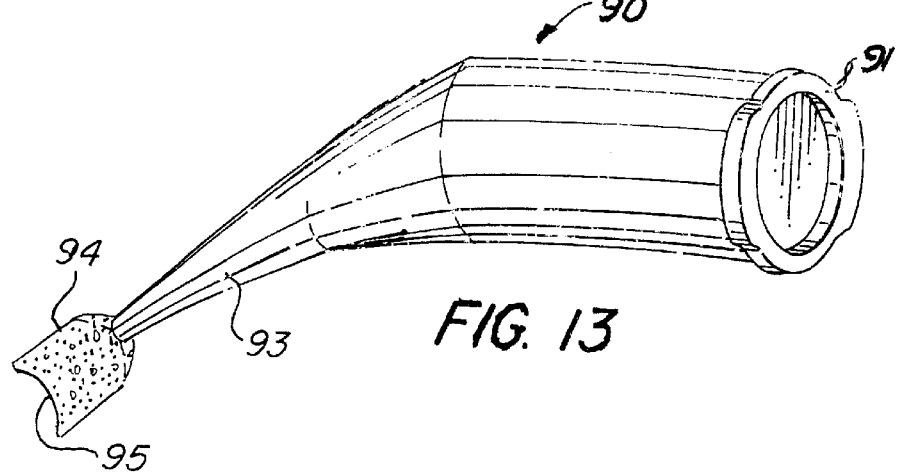
FIG. 13 is a perspective view of yet another embodiment of the present invention.

FIG. 13 illustrates yet another embodiment of the present invention. In this embodiment, tip, cartridge or capsule 90 has a Luhr type locking flange 91 on one end and a discharge nozzle 93 connected to the other end. Attached to the discharge nozzle 93 is a foam or porous flow through applicator 94 having a concave portion 95 to conform to the shape of a tooth whereby the dental material dispensed therethrough may be spread or brushed onto a tooth in broad strokes.

Figure 14:
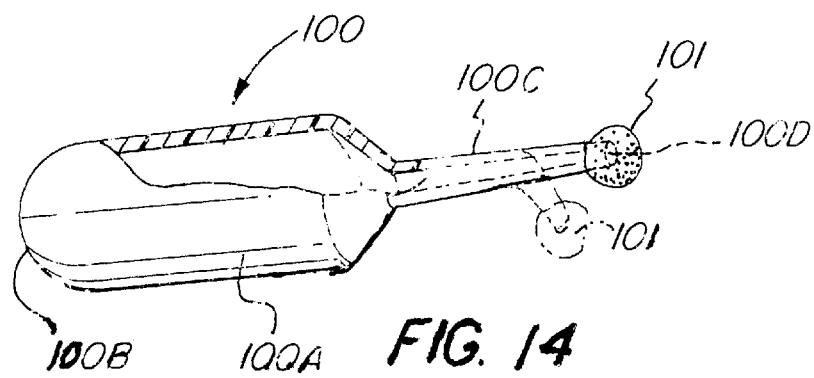
FIG. 14 is a partially sectioned view of another embodiment of the present invention.

FIG. 14 illustrates yet another embodiment of the present invention directed to a sealed dental container or ampule that is squeezable. The dental container or ampule 100 has a body portion 100A, which is closed at one end 100B. The other end terminates in an elongated discharge nozzle 100C having a distal end which is also initially sealed. The body 100A of the ampule 100 is preferably formed of a flexible plastic material whereby the body portion 100A functions in the nature of a squeeze bottle. Disposed within the body portion 100A is a predetermined amount of low viscosity dental material. The dental material may be a fluent gel or liquid. The discharge nozzle 100C is flexible and may be bent into a desired position as illustrated in phantom in FIG. 14. Covering the discharge end of the discharge nozzle 100C is a foam or porous flow through cover or applicator 101 in the form of a ball. The closed or sealed end 100D of the discharge nozzle 100C may be pieced by a suitable piecing tool to form a discharge orifice through which the dental material may be dispensed as it flows through the porous cover 101.

Figure 15:
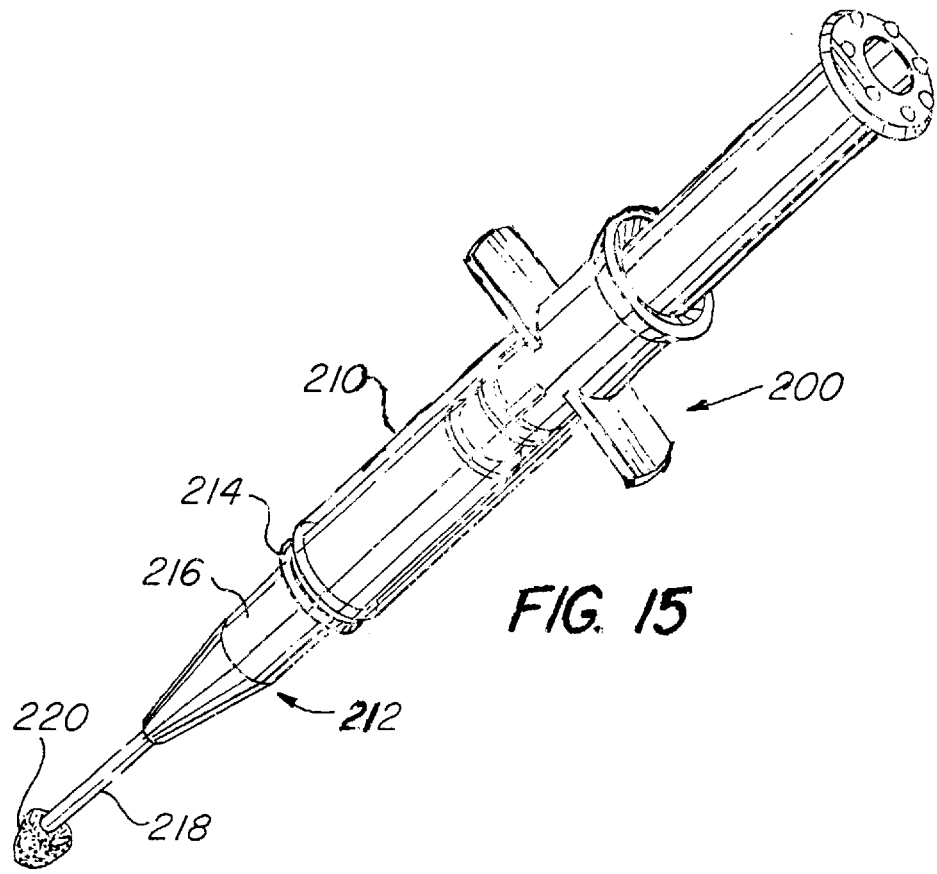
FIG. 15 is a perspective view of a syringe assembly illustrating an embodiment of the present invention.

FIG. 15 illustrates another embodiment of the present invention. In this embodiment a syringe assembly 200 comprises a syringe body 210 with an attached replaceable cartridge or tip 212. The tip 212 comprises a locking flange 214, a body portion 216, a small discharging tube or cannula 218 provided with a discharge orifice. Surrounding the discharge orifice is a foam or porous flow through applicator 220. The locking flange 214 is adapted to attach the tip 212 to the open or discharge end of the syringe 210. This permits the dispensing of bulk low viscosity material placed within the syringe 210 with the use of multiple individual tips 212. Therefore, the bulk material may be dispensed in small quantities at different times through the replaceable tips 212. At each different time or use of the syringe 210, a new applicator tip 212 may be used. It will be understood that the tip 212 may be secured to the syringe by various means, such as press fit, screw threads, bayonet fittings, Luhr locking flange, and/or other equivalent attaching systems.

It should be appreciated that the present invention provides a dental material container, capsule, nozzle or ampule with a flow through applicator having improved flow control characteristics enabling low viscosity material to be dispensed. Additionally, the foam or porous flow through applicator of the different embodiments takes a variety of shapes. Each of the shapes may be molded as desired during the manufacturing process of the tip, cartridge, capsule or container. Alternatively, the foam or porous flow through cover or applicator may be adhered to the tip, cartridge, capsule or container by suitable adhesives and/or mechanically attached. The present invention having a foam applicator end can be easily manufactured and provides for a more consistent and controllable flow characteristic than prior known brush or flock type applicators. Additionally, the foam or porous flow through applicator ends of the various embodiments of the present invention provides for a more consistent applicating surface and which imparts a cushioning effect to prevent scratching or damaging the surface on which the material is being applied. Therefore, the present invention in its various embodiments provides a considerable improvement over applicators previously known and used.

While the present invention has been described with respect to various dental type embodiments, other modifications, variations and uses thereof may be made without departing from the spirit and scope of this invention.

What is claimed is:

1. A dental material dispensing device for dispensing and applying low viscosity dental materials comprising:

a body portion adapted to receive and dispense a low viscosity dental material;

a flange attached to an end of said body portion, whereby said body portion is capable of attaching to a syringe;

a metal cannula attached to said body portion, said metal cannula formed of a ductile metal which can be bent to form a desired angle relative to a longitudinal axis of said body portion;

a discharge nozzle formed on an end of said metal cannula and having a discharge orifice; and a porous flow through applicator attached to said discharge nozzle and an exterior portion of said metal cannula adjacent said discharge nozzle, said porous flow through applicator completely covering said discharge orifice through which the dental material is dispensed from said discharge nozzle and through said porous flow through applicator and by which the dental material may be spread, painted or brushed directly onto a dental surface as the dental material is being dispensed.

2. A dental material container as defined in claim 1 wherein:

said porous flow through applicator is glued to said discharge nozzle adjacent said discharge orifice.

3. A dental material container as defined in claim 1 wherein:

said porous flow through applicator is mechanically attached to said discharge nozzle at said discharge orifice.

4. A dental material container as defined in claim 1 wherein:

said porous flow through applicator is molded onto said discharge nozzle adjacent to said discharge orifice.

5. A dental material container as defined in claim 1 wherein:

said porous flow through applicator is spherical in shape.

6. A dental material container as defined in claim 1 wherein:

said porous flow through applicator is generally cylindrical in shape.

7. A dental material container as defined in claim 1 wherein:

said porous flow through applicator is conical in shape.

8. A dental material container as defined in claim 1 wherein:

said discharge orifice being outwardly flared to form a retainer, said porous flow through applicator having a complementing shaped internal cavity adapted to receive said retainer, whereby said porous flow through applicator is mechanically retained on said discharge nozzle.

9. A dental material container as defined in claim 8 further comprising:

a layer of adhesive placed on said discharge nozzle for assisting in retaining said porous flow through applicator on said discharge nozzle.

10. A dental material container as defined in claim 1 wherein:

said discharge nozzle comprises a metal cannula.

11. A dental capsule for dispensing and applying a low viscosity dental material comprising:

a tubular body defining a reservoir and having an open end and a discharge end;

a flange attached to an end of said tubular body, whereby said tubular body is capable of attaching to a syringe;

a metal cannula connected to said discharge end of said tubular body, said metal cannula having a discharge orifice and formed of a ductile metal which can be bent to form a desired angle relative to a longitudinal axis of said tubular body;

a shaped foam flow through applicator attached to said metal cannula and completely covering said discharge orifice; and a displaceable piston adapted to fit within the open end of said tubular body to seal said open end, a low viscosity dental material adapted to be placed in said reservoir to be dispensed through said shaped foam applicator when said piston is advanced within said tubular body whereby said foam applicator is used to spread, paint, or brush the low viscosity dental material directly onto a dental surface as the low viscosity dental material is being dispensed from said reservoir.

12. A dental capsule in defined in claim 11 wherein:

said foam applicator is glued to said cannula.

13. A dental capsule as defined in claim 11 wherein:

said foam applicator is mechanically attached to said cannula.

14. A dental capsule as defined in claim 11 wherein:

said foam applicator is molded integrally to said cannula.

15. A dental material dispensing device for dispensing and applying low viscosity dental materials comprising:

a body portion defining a reservoir, said body portion having a full open end at one end adapted to receive and dispense a low viscosity dental material;

a flange circumscribing said full open end of said body portion, whereby said body portion is capable of attaching to a syringe;

a cannula attached to the other end of said body portion, said cannula formed of a ductile material which can be bent to form a desired angle relative to a longitudinal axis of said body portion;

said cannula defining a discharge nozzle at said other end of said body portion, said discharge nozzle having a discharge orifice; and a porous flow through cover connected to said discharge nozzle adjacent said discharge orifice, whereby said porous flow through cover completely covers said discharge orifice through which the dental material is dispensed from said discharge nozzle and flows through said porous flow through cover and by which the dental material may be spread, painted or brushed directly onto a dental surface as the dental material is being dispensed.

* * * * *